United States Patent
Shani et al.

(10) Patent No.: US 6,685,635 B2
(45) Date of Patent: Feb. 3, 2004

(54) NON-INVASIVE METHOD AND APPARATUS TO DETECT AND MONITOR EARLY MEDICAL SHOCK, AND RELATED CONDITIONS

(75) Inventors: Haim Shani, Shaham (IL); Ittai Shavit, Nahariya (IL)

(73) Assignee: Cardiosense Ltd., Nesher (IL)

( * ) Notice: Subject to any disclaimer, the term of this patent is extended or adjusted under 35 U.S.C. 154(b) by 6 days.

(21) Appl. No.: 10/056,064

(22) Filed: Jan. 28, 2002

(65) Prior Publication Data

US 2002/0115935 A1 Aug. 22, 2002

Related U.S. Application Data

(63) Continuation-in-part of application No. PCT/IL00/00443, filed on Jul. 25, 2000.

(30) Foreign Application Priority Data

Jul. 26, 1999 (IL) ................................................ 131108
Aug. 4, 1999 (IL) ................................................ 131245

(51) Int. Cl.[7] ............................. A61B 5/00; A61B 6/00; G01J 3/46
(52) U.S. Cl. ........................ 600/306; 600/476; 356/425
(58) Field of Search ................................ 600/306, 476, 600/549, 587; 382/128, 130; 356/402, 425

(56) References Cited

U.S. PATENT DOCUMENTS

| | | | |
|---|---|---|---|
| 3,698,382 A | | 10/1972 | Howell |
| 4,213,462 A | * | 7/1980 | Sato ........................... 600/477 |
| 4,423,736 A | * | 1/1984 | DeWitt et al. ............... 600/306 |
| 4,494,550 A | | 1/1985 | Blazek et al. |
| 4,723,554 A | * | 2/1988 | Oman et al. ................. 600/306 |
| 5,050,613 A | | 9/1991 | Newman et al. |
| 5,241,468 A | * | 8/1993 | Kenet .......................... 382/128 |
| 5,836,872 A | * | 11/1998 | Kenet et al. ................. 600/306 |
| 5,963,333 A | * | 10/1999 | Walowit et al. ............. 356/425 |

OTHER PUBLICATIONS

Schriger et al, Defining Normal Capillary Refill: Variation with Age, Sex and Temperature, Sep. 1988, Annals of Emergency Medicine, 17:9, pp. 932–935.*

* cited by examiner

Primary Examiner—Eric F. Winakur
Assistant Examiner—David J. McCrosky
(74) Attorney, Agent, or Firm—Browdy and Neimark, P.L.L.C.

(57) ABSTRACT

A diagnostic medical instrument adapted to determine whether a patient is suffering from a pre-shock, shock, or shock-related condition. The instrument is used in a capillary filling time CFT test procedure in which a skin area in the patient which overlies blood-filled capillaries which normally display a pink color is depressed to expel blood from the capillaries and impart white color to the skin at which point the pressure is released to permit blood to flow back into the capillaries and cause the skin to regain its pink color. The instrument includes a color sensor trained on the sign area and responsive to light reflected therefrom to produce a first signal at the point in time the skin color turns from pink to white and to later produce a second signal at the point in time at which the skin color has turned from white to pink. The time elapsing between the first and second signals is measured to provide a CFT index indicative of the patient's condition.

36 Claims, 5 Drawing Sheets

NON-INVASIVE METHOD AND APPARATUS TO DETECT AND MONITOR EARLY MEDICAL SHOCK, AND RELATED CONDITIONS

CROSS-REFERENCE TO RELATED APPLICATIONS

The present application is a continuation-in-part of prior PCT application no. PCT/IL00/00443, file Jul. 25, 2000, designating the United States and in which Demand was filed on Feb. 19, 2001, electing the United States, published in English under PCT Article 21(2) and now abandoned.

FIELD OF THE INVENTION

This invention relates generally to the diagnosis of medical shock-related conditions and to instruments for this purpose. More particularly, the invention relates to methods and apparatus for the non-invasive detection of pre-shock, shock and shock-related conditions (other related causes of cardio-pulmonary distress), and for assisting in a patient's recovery from these conditions by monitoring changes in capillary flow in skin areas of peripheral body organs.

BACKGROUND OF THE INVENTION

The normal skin color at most sites on the human body is generally pink. Skin color depends on the amount of blood flowing in the capillaries through which blood flows from the arterioles to the venules. The present invention resides in non-invasive detection of hemodynamic changes in the skin arteriolar-capillary flow during states of pre-shock, shock and cardio-pulmonary distress. These changes are indicative of a reduction in blood delivery to an organ of the body.

Expressed in its simplest terms, shock is the consequence of an inadequate delivery of blood to a major organ of the human body. Unless shock is promptly treated, this deprivation of blood may give rise to a disturbance in the metabolism of the organ with a resultant damage thereto. Because of the serious consequences of shock, its detection and treatment is regarded medically as an emergency procedure in which time is of the essence.

Cellular damage to an organ may be reversed by prompt treatment of shock. But it is otherwise irreversible and may lead to the death of the patient. Recovery from shock therefore depends on the promptness of treatment. However, before a patient can be treated for shock he must first be diagnosed to determine whether the patient is actually experiencing shock.

The treatment to be administered to a patient in shock depends on the nature of his condition. For example, for some shock conditions the appropriate treatment includes fluid resuscitation and the drug dopamine which acts to increase arterial perfusion pressure. Treatment for a shock condition must be administered with extreme care while the patient is being monitored.

A significant aspect of diagnostic instrumentation in accordance with the invention is that it is adapted to monitor as well as to detect shock-related conditions in a non-invasive manner. Using this instrumentation, one can make, even in a pre-hospital setting, an early diagnosis of shock as well as determine whether the drug being administered to a patient in shock is having the desired therapeutic effect.

Medical authorities classify shock syndrome in the follow five categories:

(1) Hypovolemic shock
(2) Septic shock
(3) Cardiogenic shock
(4) Obstruction to cardiac filling shock
(5) Neurogenic shock Hypovolemic shock, the most common type of shock, is caused by a massive loss of blood, plasma or fluid from the body of a patient, or the loss of fluid from an intravascular compartment. Such losses may be due to dehydration, vomiting, diarrhea, burns, or because of the abusive use of diuretics. A loss of blood and plasma is experienced in hemorrhagic shock such as in cases of blunt and penetrating trauma injuries, gastrointestinal bleeding, or Gynecologic/Obstetric bleeding. Many cases of bleeding are occult (e.g. slow internal bleeding), and therefore can not be diagnosed early.

Septic shock is caused by bacterial infection in which an endotoxin is released into the blood stream. The sequestration and pooling of blood in various vascular compartments reduces the availability of blood for the perfusion of other vital organs.

Cardiogenic shock is usually attributed to a massive myocardial infarction caused by extensive damage to the myocardium. This may be the result of arrhythmia in a patient suffering from heart disease. In this category of shock syndrome, the heart fails to pump properly, with a consequent reduction in arterial blood.

Obstruction to cardiac filling shock takes place when this filling activity is lessened or arrested by a massive pulmonary embolism, or by space-occupying lesions. Neurogenic shock results from a severe spinal cord injury, or from a massive intake of a depressant drug, causing a loss of vasometric tone.

The five categories of shock syndrome each represent other causes of cardio-pulmonary distress, or a shock-related condition. The term "shock-related condition", as used hereinafter, is ended to embrace all five categories.

The onset of a shock condition is characterized by the reduction in blood flow to skin tissue (decreased skin perfusion). This reduction in skin perfusion is the result of a profound vasoconstriction of the skin tissue arterioles, which leads to decreased capillary flow, and a resultant poor perfusion to the skin. In order to diagnose an early stage of shock, one must detect this early reduction in skin capillary flow. A useful clinical, bed-side test for poor skin perfusion is an estimation of Capillary Filling Time (CFT). When applying pressure onto a specific skin area, the capillaries below the depressed area collapse and blood is blanched therefrom, hereby causing the skin color in the depressed skin area to whiten. Upon abrupt release of this pressure, blood flows back into the capillaries and the original skin color is recovered.

CFT is defined as the time it takes for the original pink skin color to return after it had been blanched. In clinical practice, prolongation of the CFT for more than 2 second is considered a state of shock resulting from poor skin perfusion. This well-known bed-side test, although subjective and inaccurate, is an important vital sign of a shock state. If an appropriate treatment has not been given early enough, the shock condition will continue to deteriorate, the arteriolar vasoconstriction will increase even further, as reflected by prolongation of the CFT, blood pressure will fall, and the patient may die. However, an appropriate prompt treatment at the early stage of shock will decrease vasoconstriction and shorten the CFT.

Known non-invasive methods to diagnose shock do not evaluate perfusion. These methods rely on the following cardiovascular parameters:

Blood pressure. An indirect parameter of shock. The measurement of blood pressure identifies shock only in its late stages when blood pressure drops (uncompensated shock).

Heart rate. An indirect parameter of shock. The specificity of this measurement is low because heart rate is also increased by other common physiological conditions, such as anxiety and pain.

The advantage gained by measuring the rate of blood perfusion by way of CFT instrumentation is that it enables early detection of a shock syndrome (compensated shock, prior to the reduction of blood pressure) and indicates its severity. This makes possible prompt treatment of patients who can then survive a shock-related condition which may be fatal if untreated or if treated too late.

Disclosed in U.S. Pat. No. 3,698,382 is an apparatus for measuring veno filling time which applies intermittent and uniform pressure to the skin of a patient. This instrument which measures capillary flow changes secondary to the compression of a vein comprises a light source or illuminating a skin area and photoelectric monitoring means sensitive to the coloration of the skin area. The instrument measures the rate at which color returns to the skin area after pressure thereon is released. However, there are major differences between the '382 apparatus and apparatus in accordance with the invention in that the former measures capillary flow changes resulting from mechanical pressure applied to a nearby vein and these changes in flow do not reflect a state of shock.

When measuring CFT it is essential that pressure be applied only to capillary vessels while maintaining normal blood flow. In a preferred embodiment of an apparatus in accordance with the invention, a programmable mechanical unit applies an accurate measurable amount of pressure to the skin.

In order to diagnose the condition of shock, one must detect capillary flow changes resulting from the physiologic stress of shock. These changes in capillary flow are due to vasoconstriction and are not related to mechanical pressure applied to a nearby vein. When measuring CFT, it is vital that pressure be applied only to the capillary vessels while maintaining normal venous flow. In contradistinction to the apparatus in the '382 patent, an apparatus in accordance with the invention uses a programmable mechanical unit that applies accurate measurable pressure to the skin, which increases gradually, until a point of maximal skin whitening has been detected. This technique makes it possible to find the MINIMAL blanching pressure which results in maximal whitening. At minimal blanching pressure, blood is moved away from the capillaries while maintaining normal flow in the veins. This technique is the hallmark of measuring true systemic changes in capillary flow.

The '382 patent apparatus is subject to interference from external light sources and therefore requires an opaque housing for the monitoring apparatus. The apparatus does not measure skin temperature which has an independent effect on capillary flow. In addition, the mechanical arrangement required for maintaining uniform pressure in order to attain more accurate readings is cumbersome and costly.

They are also relatively complex and expensive and difficult to interpret clinically (laser Doppler devices for example). Time is of the essence in the diagnosis and treatment of shock, yet known types of skin capillary flow instrumentation are incapable of facilitating rapid diagnosis and treatment of shock. It is vital that skin capillary flow instruments have a high order of accuracy so that their readings indicate the severity of the shock or shock-related condition.

Studies published in the medical literature over the last two years demonstrate that ski temperature independently influences the skin capillary flow. One major limitation of prior skin capillary flow measurement devices is that they do not take into account skin temperature, and therefore do not correlate the measurement to skin temperature. This correlation enables real-time analysis of the state of shock. In contradistinction, a device in accordance with the invention measures skin temperature prior to each CFT measurement so that every CFT measurement is correlated to the change in skin temperature.

Of general background interest is U.S. Pat. No. 4,494,550 which discloses apparatus for the non-invasive detection of venous and arterial blood flow drainage disorders which is designed for the detection of flow abnormalities in the large vessels of a limb. Also of background interest is U.S. Pat. No. 5,050,613 (1991) which discloses a vascular testing apparatus. This includes capillary blood flow sensors to measure the blood flow of a patient. This diagnostic tool acts to determine the overall vascular integrity of a patent, but is unable and does not diagnose shock or shock-related conditions

SUMMARY OF THE INVENTION

In view of the foregoing, the main object of this invention is to provide a diagnostic method and an instrument for carrying out the method to determine accurately whether a patient is suffering from a state of shock and shock-related conditions, as well as to measure and monitor the severity of this physiologic condition.

In particular, an object of this invention is to provide a non-invasive method and apparatus adapted to detect pre-shock, shock and shock-related conditions by ongoing measurements of the patient's capillary filling time (CFT).

A significant advantage of an apparatus in accordance with the invention is that it can expedite recovery by monitoring changes in capillary flow in skin areas of peripheral body organs. The CFT measuring instrument provides a rapid yet accurate reading of the patient's condition, making it possible to treat the patient without delay to avoid damaging consequences.

It is also an object of this invention to provide a CFT diagnostic instrument which is of relatively simple design and easy to operate.

Briefly stated, these objects are attained in a diagnostic medical instrument adapted to determine whether a patient is suffering from a pre-shock, shock, or shock-related condition. Some shock-related conditions are related to inadequate flow in a specific organ. These medical conditions are common in patients after orthopedic surgery, flap reconstruction surgery, or patients who suffer from a severe peripheral vascular disease. By being highly sensitive to changes in capillary flow, an apparatus in accordance with the invention is applicable to these medical shock-related conditions.

The instrument is used in a capillary filling time test procedure in which a skin area in the patient overlying blood-filled capillaries which normally display a pink color, is depressed to expel blood from the capillaries and to blanch the skin and impart a white color thereto. When a point of blanching has been attained at a minimal pressure point, the pressure is then released to permit blood to flow back into the capillaries and cause the skin to regain its natural pink color. Using this minimal blanching pressure technique, blood is withdrawn from the capillaries whereas venous blood flow remains almost intact.

The instrument includes a color sensor trained on the skin area and responsive to light reflected therefrom to produce a first signal at the point in time the depressed skin color is blanched from pink to white and pressure is released when blanching at minimal pressure is attained, to later produce a second signal at the point in time at which the skin color regains its natural pink color. When the post-blanching skin color corresponds to a pre-test natural color, the CFT can be detected by recording the time which has elapsed from the maximal blanching point to this final point. In other words, the time elapsing between the first signal (starting point of minimal blanching pressure release) and the second signal (final point where post-blanching color equals pre-test color) is measured to provide a CFT index indicative of the patient's condition at the time the test was conducted.

For each pre-determined time interval, this measurement is repeated and a new CFT is recorded.

The device will continue measuring CFT every 30 seconds to 1–5 minutes (this depends on clinical demands), and a change of CFT over time will be recorded and monitored. This change in CFT, or d[CFT]/d[t], reflects skin perfusion changes over time and measures deterioration or improvement of shock state.

In one preferred embodiment of the invention, the color sensor includes a video camera trained on the skin area of the patient and responsive to light reflected from this area to yield an image signal whose character depends on the existing color of the skin.

In another embodiment, the skin area is illuminated by a beam of light modulated at a predetermined frequency, the pulsed light reflected from this area being intercepted by a photosensor whose output signal is indicative of the skin color.

BRIEF DESCRIPTION OF THE DRAWINGS

For a better understanding of the invention as well as other objects and features thereof, reference is made to the annexed drawings wherein.

DETAILED DESCRIPTION OF THE INVENTION

Figure 1A:
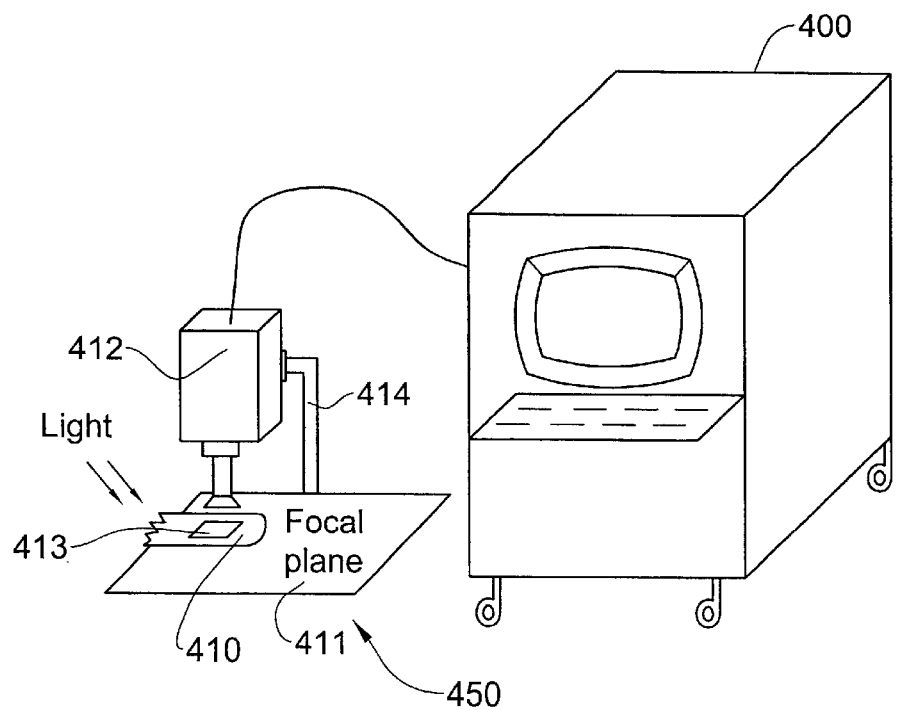
FIG. 1A illustrates the structure of a skin color sensing apparatus for the diagnosis of a shock-related condition in a patient by measuring the capillary filling time and rate in accordance with a first embodiment of the invention.

First Embodiment: Schematically illustrated in FIG. 1A is a CFT instrument 450 adapted to diagnose a shock-related condition in a patient by measuring capillary filling time and rate.

Instrument 450 includes a camera 412, such as a color video camera, fixed in place by a holder 414 above a rigid table surface 411 on which an appendage 410 of a patient rests. This appendage may for example be the patient's finger. The position of camera 412 is adjusted so that the skin area 413 viewed by the camera for purposes of CFT measurement, is in or is close to the focal plane of the lens. Pressure may be applied to and released from skin area 413 manually or by using mechanical apparatus which may be automatically controlled.

Skin area 413 is illuminated by background light, and light reflected from the surface of this area is received in the lens of camera 412. A minimal illumination level of 0.2 lux is sufficient for most currently-available modern cameras for color discrimination. Camera 412 generates an electrical signal having a magnitude corresponding to the particular color of the image received by the camera, this signal being fed by a line to a processing and display unit 400. In the event the illumination level of the background light is insufficient, skin area 413 may be illuminated with a light source, such as a conventional lamp or a Light Emitting Diode (LED).

Figure 1B:
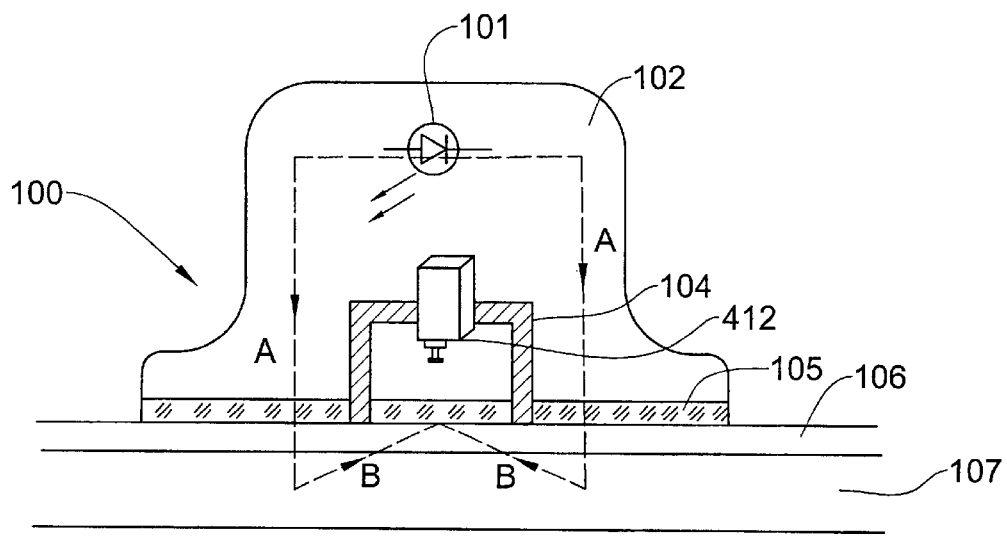
FIG. 1B schematically illustrates the color sensor included in the apparatus shown in FIG. 1.

A sensing device 100 as shown in FIG. 1B, is connected to the processing and display unit 400 by an electrical cord through which CFT data is fed for processing and display. The processing and display unit 400 may be a personal computer that uses control and processing software to process the data received by the lens of camera 412, and calculate the CFT total time and rate. Pressure is applied and released manually by the user in accordance with instructions provided by processing and display unit 400. The processing and display unit 400 may further include circuitry for controlling automated application of pressure.

The control circuitry may also be used to select a specific area for processing taken from the imaged skin area. Such selection may be carried out, for example, by software which controls the processing. The sensing device may also be attached to other locations in the patient's body that are rich in subcutaneous blood vessels, such as to the lip or to the ear lobe, for measuring the CFT.

FIG. 1B schematically illustrates the structure of a skin color sensing device 100 for the diagnosis of a shock-related state in a patient by measuring the capillary filling time and rate. Device 100 comprises a camera 412, such as a color video camera, contained in a transparent external housing 102, whereby most of the background light enters through is external housing and illuminates the skin surface 106.

Device 100 may further include an optional light source 101, such as an LED, operated by a power supply during measurement when background illumination is not at a level sufficient to enable the camera 412 to discriminate between colors. Eternal housing 102 may be light reflecting with an opening in its bottom side, so that most of the light radiation emitted from light source 101 is directed toward the bottom side in one direction "A".

External housing 102 may also include an opaque internal housing 104, having an opening in its bottom side, so as to enable light radiation to enter into the opaque internal housing space only from its bottom side. Using this structure, camera 412 in internal housing 104 receives most of the light reflected from the skin. The bottom sides of external housing 102 and internal housing 104 are aligned with each other and covered by a transparent rigid layer 105. Layer 105 acts to apply pressure on the skin while enabling light to pass through in both directions.

Transparent rigid layer 105 is brought into contact with an exterior layer 106 of the skin of the patient being diagnosed.

Pressure is applied manually or automatically on the external housing 102 toward the skin surface in a perpendicular direction A. External housing 102 delivers the pressure to the transparent rigid layer 105, which transfers it through exterior layer 106 to the interior layer 107 of the skin containing most of the subcutaneous blood vessels (capillaries). When the magnitude of applied pressure is adequate for expelling blood from the capillaries and maintained for a sufficient period of time, blood is forced out of the capillaries and the color of the interior layer 107 of the skin becomes much brighter (i.e. close to white).

The background light as well as light radiation emitted from light source 101 penetrates the skin and is partially reflected back in direction "B" into internal housing 104. The degree of reflection from interior layer 107 is inversely related to the blood flow in the capillaries under pressure inasmuch as blood absorbs light, the more blood the less the amount of reflected light. The reflected light enters the lens of camera 412, which produces an electric signal whose magnitude depends on the instantaneous color of the skin. The position of camera 412 within the device 100 is arranged so that the exterior surface of the transparent rigid layer 105 is essentially in the focal plane of the camera 412. This positioning results in a clear and focused image that is received by the camera lens. A focused image sharpens the distinction between colors and therefore enhances the resolution and accuracy of the measurement.

Under zero pressure (i.e., full blood flow), a patient's skin color is normally pink, and less light radiation is reflected back from the capillaries. When the skin is subjected to a pressure to arrest blood flow, the skin color then becomes white and more light radiation is reflected back from the capillaries. Therefore, changes in magnitude of the electric signal yielded by camera 412 affords an accurate index to capillary filling time and rate which commences upon releasing the pressure from the skin. Device 100 is connected to a power supply for operating the optional light source 101 and for operating data collection, processing and display circuitry for processing the signals provided by the camera 412 and displaying the measurement results.

Figure 2:
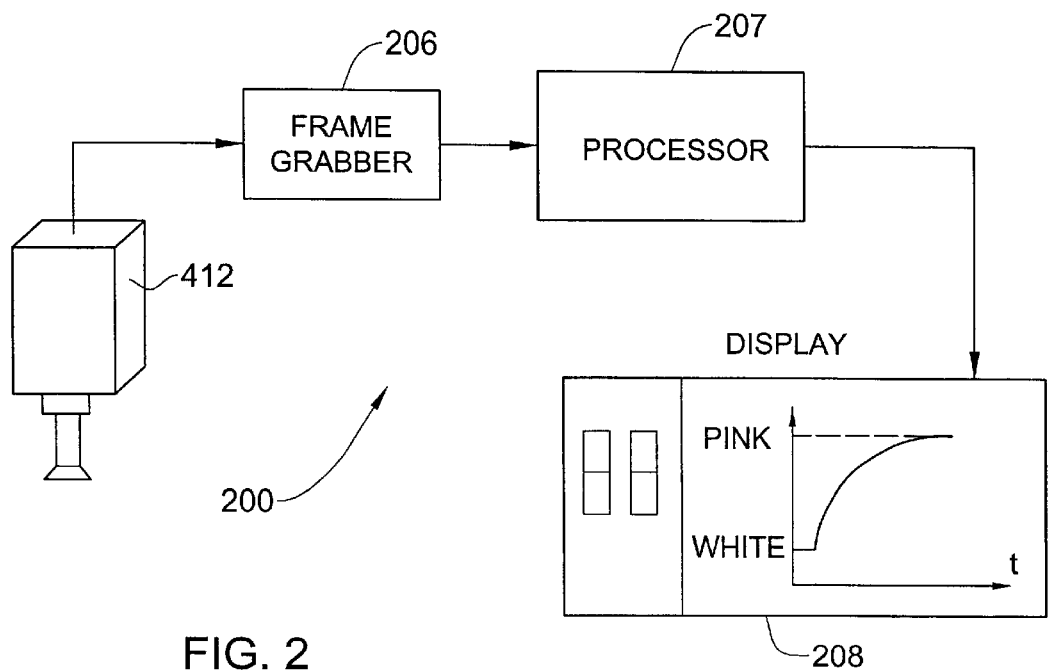
FIG. 2 is a block diagram of the apparatus shown in FIG. 1 for the diagnosis of a shock-related condition in a patient by measuring capillary filling time aid rate.

FIG. 2 is a block diagram of an apparatus 200 or the diagnosis of a shock-related state in a patient by measuring capillary filling time and rate in accordance with the invention. Apparatus 200 includes camera 412, whose output is supplied to a frame grabber 206 for capturing the image received by the camera. Light reflected from the skin surface is converted by camera 412 to a corresponding video signal, such as a Composite Video or a Red-Green-Blue (RGB) Video signal, depending on the type of camera used, that represents the received image.

The video signal is fed into an electronic circuit (e.g., a Frame Grabber or a Video Capture circuit) which decodes the video signal and converts it into a corresponding array of digital values, which array is stored in a memory. Each cell of the memory stores a digital value that represents the light intensity and the color of a portion of the received image. Camera 412 updates the image at a rate of 50 times per second, and therefore, the image information, generated by frame grabber 206 and stored in the memory array is also updated at the same rate. A rate of 50 times per second usually corresponds to video cameras compatible with Pulse Alteration by Line (PAL) video encoding standards. A rate of 60 times per second usually corresponds to video cameras compatible with National Television System Committee (NTSC) video standards. Faster video cameras to update the image at higher rates are also useable.

The digital data is fed into a digital processor 207 which analyzes the data and display the results on display 208.

Processor 207 samples a desired area of the image which contains most of the tested skin area. At the next step, processor 207 calculates the intensity of the essentially pink/red light, reflected by the tested skin area. The intensity of the rejected light is processed and normalized to a baseline, which may be the normal color of the patient's skin when no pressure is applied. The image information is updated in a rate determined by the type of camera included in the system. Processor 207 therefore continuously calculates the normalized intensity.

Display 208 presents a display of the calculated results of the normalized intensity (i.e., the CFT) as well as a graphical representation of the measurement process as a function of time. The graphical representation indicates whether or not the measurement results are reasonable, and if desired, the measurement can be repeated. Other data processed results, such as statistical data, can be also displayed to provide indications regarding the reaction of the patient to medical treatment.

Figure 3A:
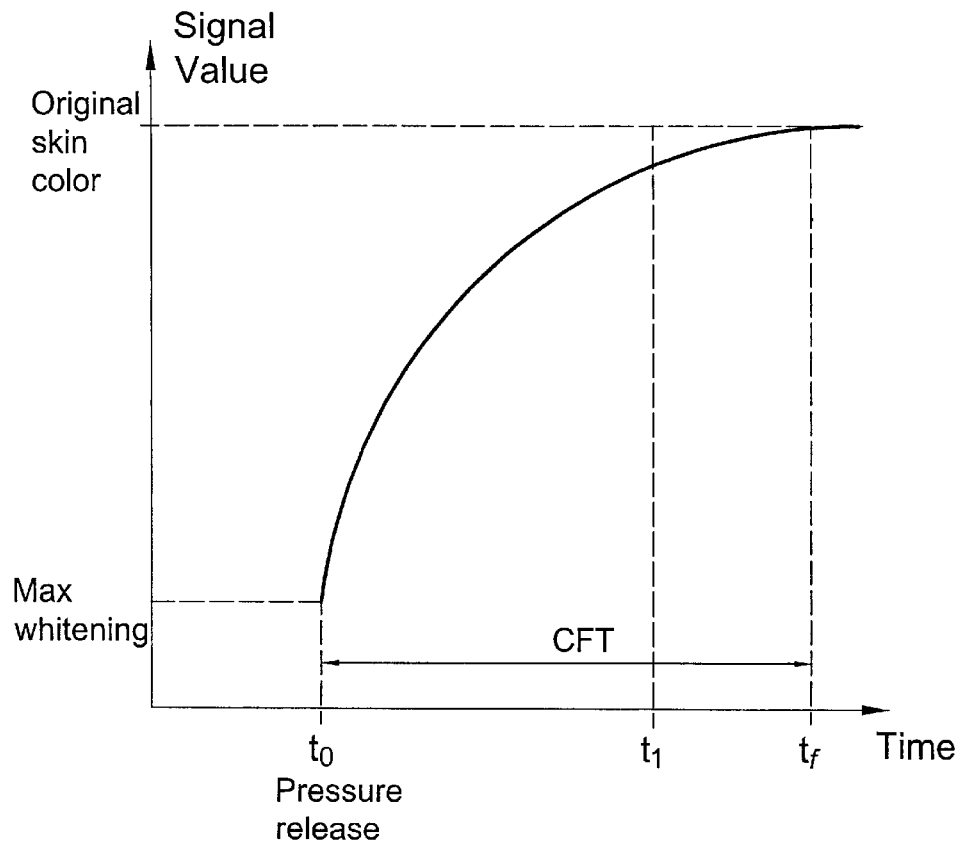
FIG. 3A is a graphical representation of the measurement CFT results.

FIG. 3A is a graphical representation of CFT measurement results. At the first stages no pressure is applied on the skin, and therefore the apparatus 200 can carry out calibration of the initial skin color of the patient. The value of the calibration is stored for use at the end of the measurement. The calibration process is essential in that the normal color of the skin depends on the individual and differs from patient to patient.

At the second stage of operation, pressure is applied to the skin at a magnitude and for a duration sufficient to obtain maximum whitening of the skin color in the depressed area. The processor can be programmed to provide a warning signal (such as a beep) to the user when the pressure is insufficient or shorter in duration than required. Obtaining maximum whitening of all the depressed area is indicative of sufficient whitening pressure.

Stronger pressures, of longer duration do not affect the skin color beyond maximum whitening. After obtaining maximum whitening, a signal indicative thereof is provided to the user to quickly release the pressure. Measurement of the CFT is started at that instant (to) at which the skin color proceeds to change from its maximum whitening color to regain its original pinkish color. Normally, the rate of filling is higher at the beginning of the filling process and lower as time lapses.

The apparatus uses the stored calibration value to determine the moment tf at which the normal pink skin color is regained, at which point the measurement ceases. The recovery time can be determined by the desired degree of measurement accuracy. For example, point tf can be defined as the instant at which the value of the digital word that corresponds to the current skin color reaches a value that is 90% of the value of the digital word that corresponds to the original skin color of the patient being diagnosed. In the graph of FIG. 3A, the CFT reading is given by tf-to.

The accuracy of the measurement can also be determined by the rate of change in the skin coloring in the time interval that is close to the conclusion of the measurement. The last segment of the graph lies between the points of time t1 and tf. The rate of change in this time interval is nearly constant and is nearly insensitive to the magnitude and duration of the applied pressure. Hence, the CFT can be extrapolated with relatively high accuracy from the time interval tf-t1. Under normal conditions CFT should be below one second. A CFT value above two seconds can be regarded as representing a pre-shock state. Longer CFT values can be considered to be indicative of more severe shock states.

Figure 3B:
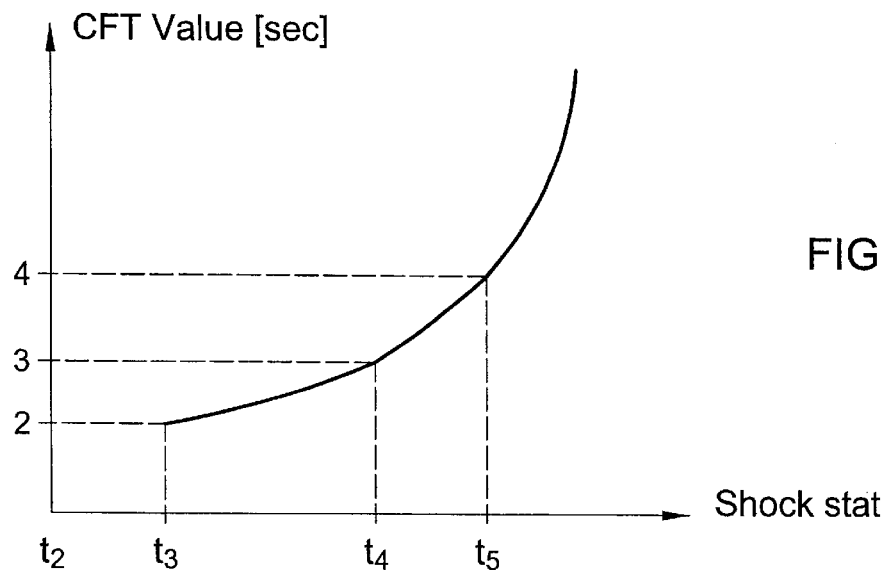
FIG. 3B is a graphical representation of CFT, as a function of the level of shock, for obtaining inferences related to the trend of the patient's physiological condition in reaction to medical treatment.

FIG. 3B is a graphical representation of the CFT as a function of shock-state for obtaining inferences related to the trend of the patient's physiological condition in response to medical treatment. In the initial time interval between time-points t2 and t3, the CFT value is then below 2 seconds, hence the patient is in a normal, shock-free condition. An early and mild shock condition starts at time-points t3 where the CFT value exceeds 2 seconds. As time lapses with no proper treatment of the shock condition, the shock becomes more severe until time-point t4 is reached. This point indicates the entry of the patient into a moderate shock condition (CFT value higher than 3 seconds). The next stage is indicated by the time-point t5. This indicates the entry of the patient into a late (severe) shock condition (CFT value higher than 4 seconds). From point t5 and beyond, the CFT rises rapidly.

Analysis of skin temperature is crucial for the clinician to make an appropriate diagnosis and monitoring of shock. For example, very cold skin temperature will independently prolong CFT (an acceptable false positive of CFT measurement). For each time interval, the device will measure and monitor both CFT and skin temperature. (See "Modified Second Embodiment" in connection with FIG. 6).

When a medical treatment is administered to the patient, the CFT is measured thereafter on a periodic basis. This measurement is used to determine whether the pre-shock or the actual shock condition is reversible. If the patient's reaction to the given treatment is positives then in time the CFT will be reduced, indicating a significant improvement in the physiological condition of the patient until the CFT value goes below the safe 2 Sec level.

Figure 4:
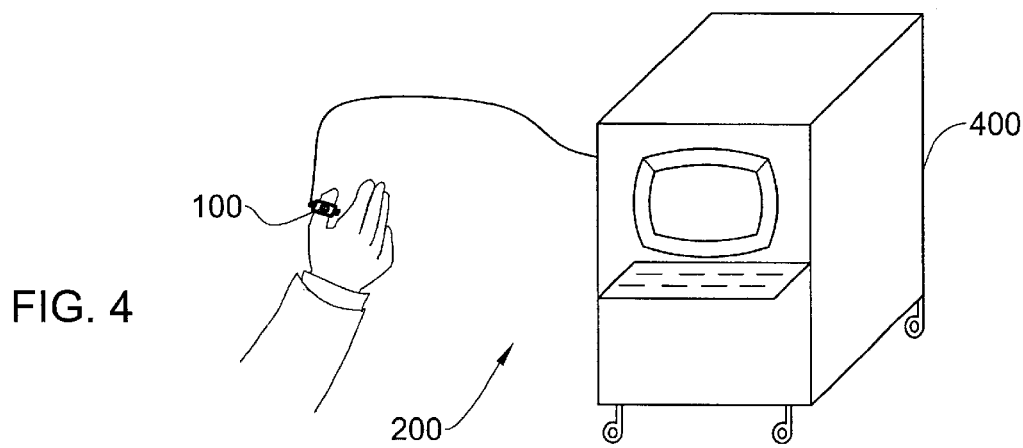
FIG. 4 schematically illustrates how the apparatus is used, as shown in FIG. 2, for the diagnosis of pre-shock state in a patient.

FIG. 4 schematically illustrates the use of an apparatus 200 for the diagnosis of pre-shock state in a patient. Apparatus 200 includes a skin color sensing device 100 attached by straps or by adhesive tape to a skin area rich in subcutaneous blood vessels, such as hand fingers, and a processing and display unit 400 coupled to sensing device 100. Device 100 is connected to the processing and display unit 400 by an electrical cord through which the CFT data is fed for processing and display. Pressure is applied and released manually by the user in accordance with instructions provided by processing and display unit 400. The sensing device for measuring CFT may also be coupled to other sites in the patient's body that are rich in subcutaneous blood vessels, such as to the lip or to the ear lobe.

In practice, an automatic measurement can be carried out by integrating a mechanical control apparatus into sensing device 100 adapted to control the applied pressure and release thereof by an external controller. Such mechanical apparatus may comprise a miniature linear motor that produces linear movement rather than rotational movement. Alternatively, linear movement pressure can be applied by an electromagnet or by a rotational motor with an eccentric movement mechanism. The linear movement can be controlled to depress a movable member, such as a movable transparent rigid layer, against the skin and to release the pressure by a corresponding control command.

Sensing device 100 and the processing and display unit 400 may further include receiving and transmitting circuits to enable wireless exchange of data and control commands required for CFT measurements. Wireless connection makes feasible a single processing and display unit 400 to control and monitor several sensing devices 100, each attached to a different patient. Each sensing devices 100 is identified by a unique code assigned to it, to eliminate false associations between processed data and a patient.

The invention can be carried out in a great variety of other ways employing techniques which differ from those described herein, such as by using pneumatic apparatus for applying pressure to the patient's skin, or by using an Infra-Red camera rather than a video camera. Also one can store the history of CFT measurements of a patient and display the variation of the CFT curve with time.

Second Embodiment: This embodiment of a CFT diagnostic instrument differs from the instrument shown in FIG. 1 mainly in the nature of its skin color sensor. However, in all other respects it operates in the same manner as does the first embodiment.

Figure 5:
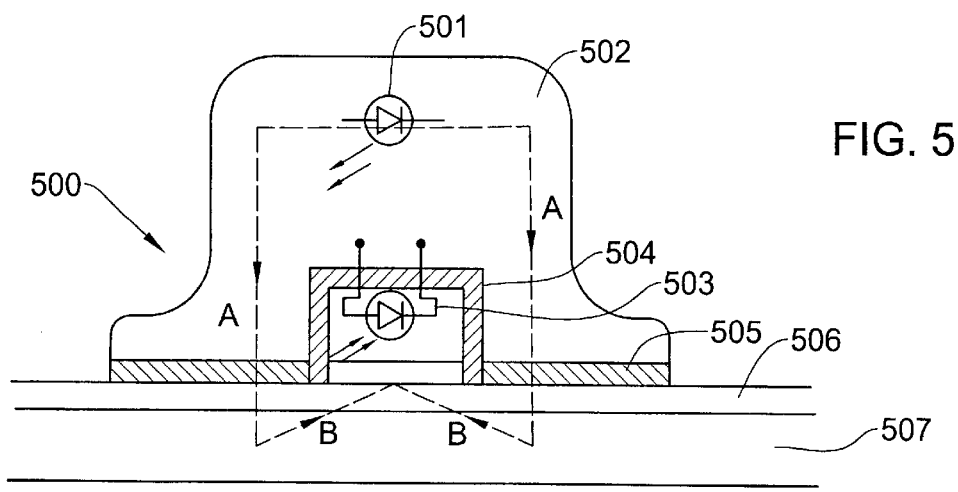
FIG. 5 illustrates the color sensor included in a second embodiment of a CFT diagnostic instrument.

FIG. 5. Schematically illustrates the structure of a skin color sensing device 500 for the diagnosis of a shock-related state in a patient by measure the capillary filling time and rate according to the second embodiment of the invention. Device 500 includes a pulsating light source 501, such as a Light Emitting Diode (LED) driven by a rectangular voltage pulse generator at a predetermined frequency fo. Light source 501 is enclosed in a light-reflecting external housing 502 having an opening in its bottom side so that most of the light radiation emitted from light source 501 is directed toward the bottom side in one direction "A". External housing 502 has within it an opaque internal housing 504 containing a light sensor 503, such as a photodiode, a phototransistor, a photo-resistor or a photoelectric cell. Internal housing 504 has an opening in its bottom side which permits light rays to enter therein only through its bottom side. The bottom sides of external housing 502 and internal housing 504 are aligned with each other and are covered by a transparent rigid layer 505. This layer serves to apply pressure on the skin while enabling light to pass therethrough in both directions.

Transparent rigid layer 505 of device 500 is pressed into contact with the exterior layer 506 of the skin. Pressure is applied manually or automatically on the external housing 502 toward the skin surface in a perpendicular direction. The external housing delivers the pressure to the transparent rigid layer 505 which transfers it through exterior layer 506 to the interior layer 507 of the skin containing most of the subcutaneous blood vessels (capillaries).

As a result, when the magnitude of the applied pressure is adequate and is maintained for sufficient period of time, blood is then forced out of the pressurized capillaries and the color of the interior layer 507 of skin becomes much brighter (i.e. substantially white). Light rays emitted from light source 501 penetrate into the skin and are partially reflected back in direction "B", into the internal housing 504. The degree of reflection from interior layer 507 is inversely related to blood flow in the capillaries under pressure inasmuch as blood absorbs light the more blood in the capillaries the lesser is the reflected light.

The reflected light is aggregated by light sensor 503 which yields an electric signal whose magnitude depends on the instantaneous color of the skin. Under zero pressure (i.e., full blood flow), the skin color is normally pink and therefore less light is reflected back from the capillaries. When the skin is subjected to pressure and blood is expelled from the capillaries, the skin color is then white. Hence when the skin is pink, the intensity of reflected light is relatively low and when the skin is white the intensity of reflected light is significantly higher. As a consequence, changes in magnitude of the electric signal produced by light sensor 503 affords an accurate measure of the capillary filling time and rate. The Device 500 is connected to a pulsed power supply for energizing light source 501 and for operating data collection, processing and display circuitry to process the signals yielded by light sensor 503 and for displaying the measurement results.

Figure 6:
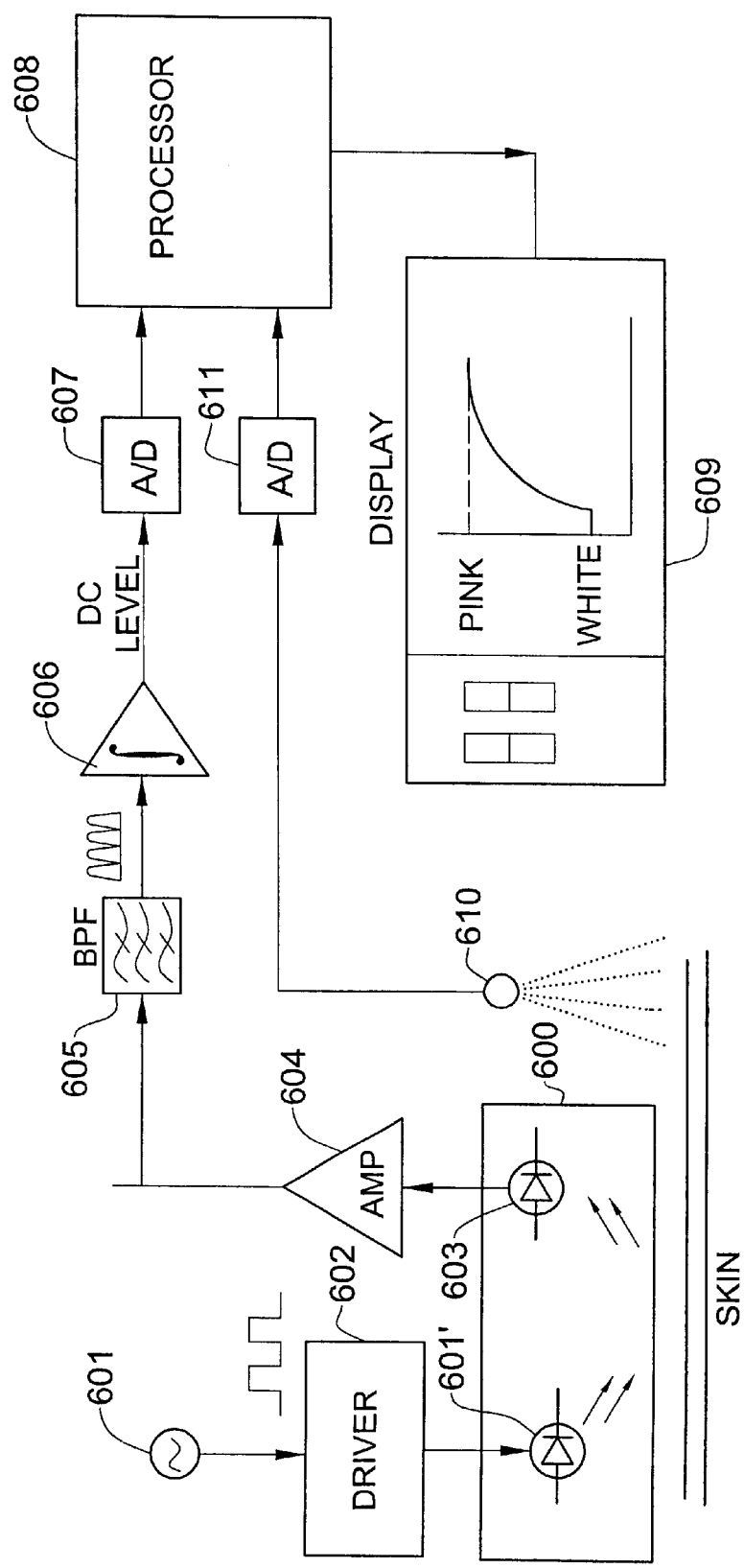
FIG. 6 is a block diagram of the apparatus included in the second embodiment.
Figure 7:
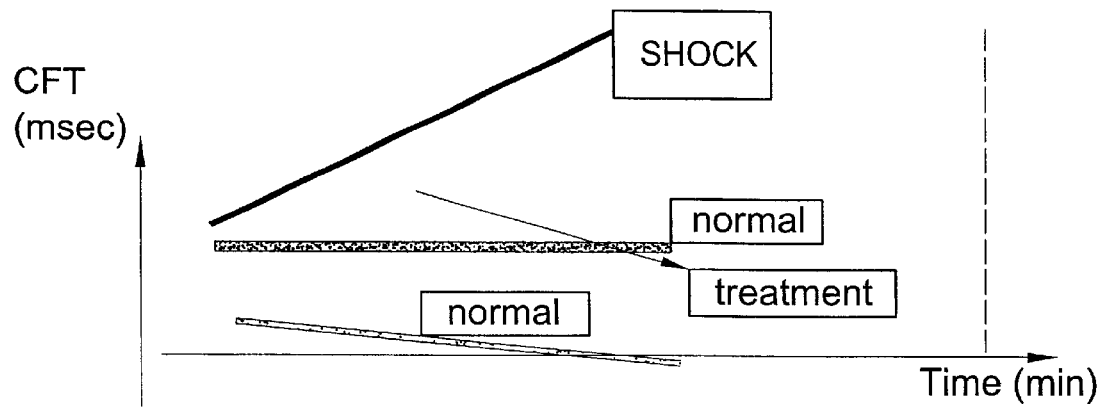
FIG. 7 is a graph showing the relationship between CFT readings and conditions of shock.

FIG. 6 is a block diagram of an apparatus 600 in the second embodiment for diagnosing a shock-related state in a patient by measuring capillary filling time and rate. Apparatus 500 comprises a rectangular pulse oscillator 601 operated at a frequency fo=18 KHz. The output of oscillator 601 is fed into a driver 602 which provides rectangular output pulses having sufficient energy to power light source 601' to emit light pulses at the same frequency fo. Light reflected from the skin is converted by light sensor 603 to a corresponding pulsatory electrical signal. The signal is fed into an amplifier 604 operating within a frequency band that includes frequency fo to increase the amplitude of the electrical signal.

Light sensor 603 is most sensitive to light radiation between red and infra-red in the color spectrum but also to background light sources, such as external light radiation which adds an unwanted 50/60 Hz signal, or to sunlight which adds an unwanted DC level. Therefore the electrical output signal includes interfering components as well as the desired component at frequency fo. The interfering components are reduced in magnitude by the amplifier 604 which is tuned to amplify the desired component at frequency fo to a greater degree than the unwanted components.

The amplified electrical signal from amplifier 604 is further filtered by a Band-Pass-Filter (BPF) 605. This filter is tuned to pass only the desired component at frequency fo and to reject all other unwanted components. BPF 605 is implemented as an active filter using Integrated Circuit (IC) technology. The resultant filtered signal at the output of BPF 605 is a rectified sine wave which is fed into an integrator circuit 606. Integrated Circuit 606 outputs a Direct Current (DC) level proportional to the magnitude of the rectified sine wave and hence the magnitude of light reflected from the skin. It is therefore highly sensitive to changes in skin color.

The DC signal is fed into an Analog to Digital Converter (ADC) 607, which converts the DC level into a corresponding digital word. The digital data is fed into a digital processor 608 which analyzes the data and display the results on a suitable display 609. Display 609 exhibits a digital value representing the measurement results (i.e., the CFT), and a graphical representation of the measurement process as a function of time. The graphical representation provides an indication of whether or not the measurement results are reasonable, and if desired, the measurement can be repeated. Other data processed results, such as statistical data, can be also displayed to provide indications related to the reaction of the patient to medical treatment.

FIG. 3A which is a graphical representation of the measurement results of the CFT obtained with the first embodiment of the invention is also representative of the results obtained with the second embodiment. At the first stage, no pressure is applied on the skin and therefore the diagnostic apparatus can carry out calibration of the initial skin color of the patient which is a shade of pink.

The calibration value is stored for use at the conclusion of the measurement. The calibration process is essential, since the normal color of the skin depends on the individual being tested and differs somewhat from patient to patient. At the second stage, pressure is applied with a magnitude and duration sufficient to obtain maximum whitening of the skin color in the depressed area. The processor can be programmed to provide a warning signal (such as a beep) to the user, that the pressure is not sufficient or is shorter in duration than required. Obtaining maximum whitening of the entire depressed area is indicative of sufficient pressure.

After obtaining maximum whitening, a corresponding signal is provided instructing the user to quickly release the pressure. Measurement of the CFT is initialed at that moment, "to". The skin coloring proceeds to change from maximum whitening to essentially the original pinkish color. Normally, the rate of filling is higher at the beginning of the filling process and lower as time lapses. The apparatus uses the stored calibration value to determine the moment tf, at which the original skin color is recovered and the measurement terminated. Recovery time can be determined in accordance with the desired measurement accuracy. For example, tf can be defined as the instant at which the value of the digital word that corresponds to the current skin color reaches a value which is 90% of the value of the digital word that corresponds to the original skin color of the patient being tested. In the graph of FIG. 3A, the CFT is given by tf-to.

The accuracy of the measurement can also be determined by the rate of change in the skin coloring, in the time interval that is close to the completion of the measurement. The last segment of the graph appears between the time points t1 and tf. The rate of change in this time interval is nearly constant, and is almost insensitive to the magnitude and duration of the applied pressure. Hence the CFT can be extrapolated with relative accuracy from the the interval tf-t1.

The CFT under normal shock-free conditions should be below 1 Sec. When a CFT value rising above 2 Sec is diagnosed. This is indicative of a pre-shock state. Longer CFT values indicate a more severe shock condition.

FIG. 3B which is a graphical representation of the CFT in the first embodiment for obtaining inferences related to the trend of the patient's physiological condition in reaction to medical treatment, is also applicable to the second embodiment.

Modified Second Embodiment: The color sensor included in the second embodiment of CFT diagnostic apparatus does not take into account the temperature of the patient's skin at the time of the diagnosis and its effect on the CFT reading. For accurate readings it is necessary to measure the skin surface temperature and record it prior to each CFT measurement.

In order to factor into the processing of the reflected light intensity the influence thereon of skin temperature, included in the color sensor shown in FIG. 6 is a heat sensor 610, such as an infrared detector or a thermistor, whose output signal varies in magnitude as a function of the intensity of infrared rays emanating from the skin surface in the course of CFT diagnosis. Infrared detector 610 is responsive only to the heat of the skin, not to light reflected from the skin surface.

The electrical signal yielded by heat sensor 610 is not pulsed and has a magnitude which is a function of skin temperature. This signal is digitized in an A/D converter 611 whose digital output is entered into computer microprocessor 608. Microprocessor 608 is programmed by software to factor into the CFT reading the effect thereon of skin temperature. This corrected reading is of value in real time diagnosis of a patient's shock-related state, for it takes into account the skin temperature of the patient when in shock. It is of somewhat lesser value when monitoring the condition of a patient being treated for shock.

A preferred form of skin temperature sensor is a thermometer which can be placed directly on the skin surface of a patient being diagnosed for shock, to provide an electrical signal whose magnitude depends on the existing skin temperature. The thermometer signal is entered into microprocessor 608 of a computer into which is also entered the CFT signal indicative in terms of seconds, the shock state of the patient.

Figure 8:
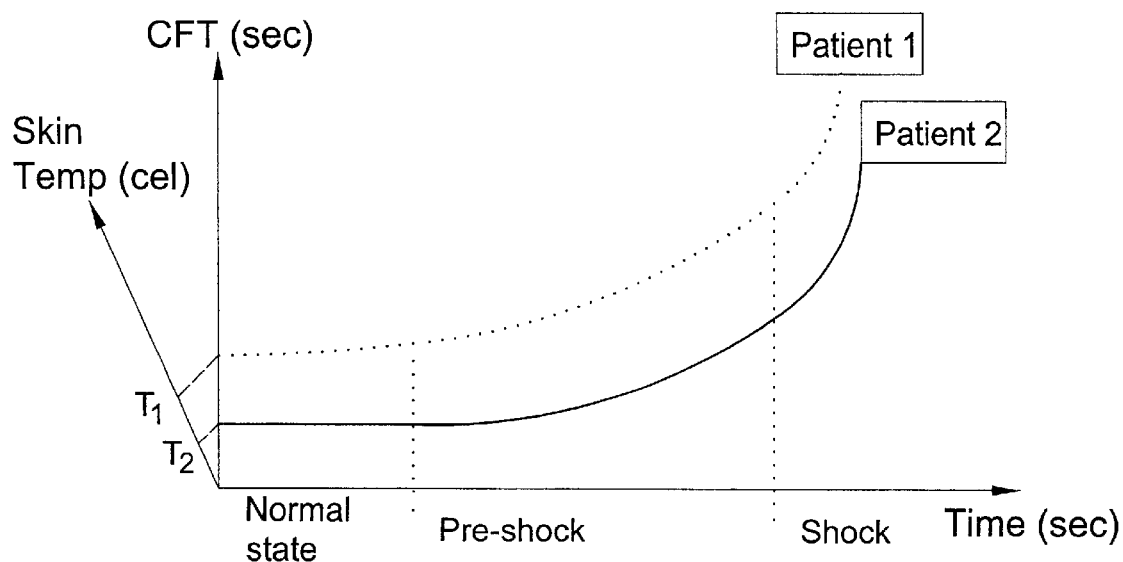
FIG. 8 is a graph showing the relationship of skin temperature on CFT readings.

FIG. 8 illustrates the effect of skin temperature on CFT readings for patients 1 and 2 having different skin temperatures T1 and T2. It will be seen that in a normal no-shock state, the CFT readings which indicate this state in terms of seconds are different, thereby reflecting the effect on the CFT readings of the degree of difference between temperatures T1 and T2. Similar differences appear for the pre-shock and shock states.

A CFT instrument in accordance with the invention is a non-invasive diagnostic tool which determines the degree to which a patient is in a state of shock, making it possible for a clinician to prescribe a treatment that may save the patient's life. This instrument affords the field of medicine with a new vital sign.

Existing vital signs (pulse rate, respiratory rate, body temperate and often blood pressure) are important signs of life. Also highly significant is a patient's CFT, for this indicates whether a patient is in shock and is in danger of losing his life.

While there has been shown preferred embodiments of CFT instrumentation, it is to be understood that many changes may be made therein without departing from the spirit of the invention.

What is claimed is:

1. A diagnostic medical instrument adapted to determine whether a patient is suffering from a pre-shock, shock or shock-related condition, the instrument being used in a capillary filling time (CFT) test procedure in which a skin area of the patient overlying blood-filled capillaries normally imparting to the skin a pink color is depressed by a pressure which is sufficient to expel blood from the capillaries while maintaining normal flow in the veins, said pressure causing the skin to blanch until the skin exhibits a white color, the said pressure being released when a point of maximum blanching is reached to permit blood to flow back to the capillaries at a rate that depends on the condition of the patient to cause the skin to regain its natural pink color; said instrument comprising:

i) means including a color sensor trained on the skin area when exposed to light to generate a signal having a magnitude which is a function of light reflected by the skin area whose intensity depends on the natural color of the skin area;

ii) means responsive to said signal before pressure is applied to the skin area to determine its natural pink color to establish a reference base for the test to follow; and iii means responsive to said signal when pressure is applied to said skin during the test to measure the time elapsing from a starting point in time when the depressed skin is at its maximum blanching value of white, and the pressure applied thereon is then released to cause the capillaries to proceed to fill with blood, to a final point in time when the skin recovers its natural pink color as established by the reference base, whereby the CFT measurement is an index to whether the patient is suffering from a shock-related condition, and to the severity of this condition.

2. An instrument as set forth in claim 1, further including a temperature sensor responsive to heat radiating from the skin area to generate a temperature signal that reflects the existing temperature of the skin area, and means to factor into the CFT measurement the temperature signal to compensate the CFT measurement for the effect of skin temperature thereon.

3. An instrument as in claim 2, in which the temperature sensor is a thermometer placed on the skin area to produce a signal whose magnitude depends on the existing skin temperature.

4. An instrument as in claim 1, wherein the color sensor means includes a video camera responsive to light reflected from the skin area to yield an image signal whose character depends on an existing skin color.

5. An apparatus as in claim 1, in which the color sensor means includes means to illuminate the skin area with modulated light from a light source, and a pulsed light reflected therefrom is intercepted by a photodetector which yields a signal that depends on an existing skin color.

6. An instrument as set forth in claim 1, further including means to apply pressure to said skin area and means to control the magnitude and/or duration of the pressure so as to apply to the skin area the minimum amount of pressure necessary to cause the skin to exhibit a white color.

7. A method for the diagnosis of a shock-related state in a patient by measuring the filling time of blood vessels subjacent to skin area of the patient, comprising the steps of:

illuminating the area which is to be gauged for color with a modulated light from a light source, filtering out background noises to obtain a base-line measurement, and determining the filling time of blood vessels in said area by comparison of a current color of the area with the base-line measurement.

8. A method according to claim 7, comprising:

i) illuminating the area having an original color with modulated light from a light source;

ii) intercepting light reflected from the area with a light sensor, said light sensor producing a first signal having a magnitude which corresponds to the color of said area, said color representing the level of reflection;

iii) filtering said first signal for rejecting unwanted signals derived from interfering light, and producing a second signal whose amplitude is proportional to the amplitude of said filtered first signal;

iv) storing the amplitude value of said second signal which corresponds to said original color;

v) applying a pressure on said area, the magnitude of said pressure and its duration is sufficient to expel blood from said blood vessels to blanch the skin, up to maximum blanching and whitening of said area; and vi) measuring the filling time of blood vessels by rapidly releasing said pressure and subsequently measuring the amplitude of the second signal and displaying the total period of time from maximum whitening at the time of pressure release until the amplitude of said second electrical signal is essentially similar to said stored amplitude value, said total period of time being indicative of a shock-related state in said patient and its severity.

9. A method according to claim 8, further comprising:

i) sampling the amplitude value of the second electrical signal at a predetermined rate during said measurement and storing said sampled values; and ii) extrapolating the capillary filling time by processing at least a portion of said stored values whenever the rate of change of the capillary filling time remains substantially insensitive to the magnitude and/or duration of the applied pressure.

10. A method according to claim 9, wherein an alert signal is provided whenever the strength and/or duration of the applied pressure be insufficient for obtaining maximum whitening.

11. A method according to claim 8, wherein the pressure is applied and released automatically.

12. A method according to claim 8, further including the step of verification of the measurement by displaying a graphical representation of the measured capillary filing time.

13. A method according to claim 8, further including the steps of:
 i) repeating the measurement of the capillary filling time at different time intervals;
 ii) storing the values of all measurements; and
 iii) displaying a graphical representation of the measured filling times as a function of time, thereby obtaining a derivative of the capillary filling time on time d[CFT]/d[t], said derivative being an indication related to the recovery or deterioration of the patient from an actual or pre-shock state.

14. A method according to claim 8, wherein the light is emitted from a LED.

15. A method according to claim 8, wherein the light is modulated by rectangular pulses at a predetermined rate.

16. A method according to claim 8, wherein the light sensor is a photodetector selected from the group consisting of a photo-diode, a photo-transistor, a photo-resistor and a photoelectric cell.

17. A method according to claim 8, wherein the second electrical signal is produced by integrating the absolute value of the filtered signal.

18. A method according to claim 8, wherein pressure is applied by means of a rigid transducer containing a light source and a light sensor, said transducer being provided with a transparent wall that engages an appendage of the patient, a controlled force being imposed on said rigid transducer toward the surface of said appendage.

19. A method according to claim 18, wherein the applied pressure is controlled by means of a motor arranged to apply a force on said transducer.

20. A method according to claim 18, wherein the applied pressure is controlled by means of an electromagnet applying a force on said transducer.

21. A method according to claim 7, wherein the blood vessels are capillaries.

22. Apparatus for the diagnosis of a shock-related state in a patient and of recovery of a patient therefrom comprising:
 i) means for illuminating a skin area of the patient to be gauged for color with a light from a light source;
 ii) means for modulating said light;
 iii) means for filtering out background noises and light to obtain a base-line measurement; and
 iv) means for comparing the color of the skin area with the base-line measurement, thereby determining the filling time of blood vessels in said area.

23. Apparatus for the diagnosis of a shock-related state in a patient and of recovery of a patient therefrom, comprising:
 i) a light source for illuminating an area of the patient's skin overlying blood vessels, said area having an original color;
 ii) means for modulating light emitted from said light source at a predetermined frequency;
 iii) a light sensor for intercepting light reflected from said area and producing a first signal having a magnitude which corresponds to the color of said area, said color representing the level of reflection from blood vessels subjacent said area;
 iv) a filter for filtering said first electrical signal and for rejecting unwanted electrical signals originating in interfering light, and for producing a second signal, whose amplitude is proportional to the amplitude of said filtered first signal;
 v) means for storing the amplitude value of said second signal which corresponds to said original color;
 vi) a transducer for applying pressure on said area, and for obtaining an amplitude of the second signal which corresponds to maximum whitening of said area;
 vii) a processor for processing data collected by said transducer and for measuring the filling time of blood vessels after releasing said pressure; and
 viii) means for graphically displaying aid processed data.

24. Apparatus according to claim 23, further including means for sampling the amplitude value of the second electrical signal at a predetermined rate during the measurement and for storing said sampled values.

25. Apparatus according to claim 24, further comprising means for automatically applying and releasing said pressure.

26. A method for the diagnosis of physiological distress in a patient and for recovery of a patient from a state of physiological distress by measuring the filling time of blood vessels underlying an area of the skin of said patient, comprising the steps of:
 acquiring an image of skin area to be gauged for color to obtain a base-line color measurement,
 and determining the filling time of blood vessels in said area by comparison of the color of at least one more additional images of the gauged skin area with said base-line color measurement.

27. A method according to claim 26, comprising the steps of:
 i) positioning image acquisition means so that an area of the skin lies substantially within the focal plane thereof;
 ii) illuminating said area having an original color with light radiation at a level enabling said image acquisition means to discriminate between colors;
 iii) acquiring an image of said area with said image acquisition means;
 iv) deriving a signal from said image, said signal representative of the color of the said area;
 v) storing the value of said signal which corresponding to said original color;
 vi) applying pressure on said area, said pressure having a magnitude and duration sufficient to expel blood out from said blood vessels, and for obtaining a signal having a value which corresponds to the maximum whitening of said area;
 vii) measuring the filling time by rapidly releasing said pressure and subsequently measuring and displaying the total period of time from maximum whitening until the value of said signal is substantially the same as said stored value; and
 viii) determining the physiological distress from said total period of time.

28. A method according to claim 27, wherein the illumination is obtained from background light.

29. A method according to claim 27, wherein the illumination is obtained from a light source.

30. A method according to claim 27, further including the step of verification of the measurement by displaying a graphical representation of the measured filling rate.

31. A method according to claim 27, further comprising:
   i) repeating the measurement of the filling time at different time intervals;
   ii) storing the values of all measurements; and
   iii) displaying a graphical representation of the measured filling times as a function of time, thereby obtaining a derivative of the capillary filling time on time d[CFT]/d[t], said derivative being an indication related to deterioration in the patient's physiological condition, or to the recovery of the patient from physiological distress.

32. A method according to claim 27, wherein the blood vessels are capillaries.

33. Apparatus for the diagnosis of physiological distress in a patient and of recovery of a patient from physiological distress in accordance with changes in color of the patient's skin in response to an applied pressure on said skin, said pressure expelling blood from blood vessels subjacent to said skin, said apparatus comprising:
   i) image acquisition means for acquiring an image of an area of the skin of said patient to be gauged for color, said image acquisition means being trained in the area so that it lies essentially within the focal plane of said image acquisition means;
   ii) means for obtaining a base-line color measurement using the acquired image data corresponding to the color of said area when essentially no pressure is applied thereto; and
   iii) means for comparing the color of said area with the base-line color measurement, thereby determining the filling time of blood vessels in said area after releasing said pressure.

34. Apparatus according to claim 33, further comprising means for illuminating the area of the skin to be gauged for coloring with light radiation at a level sufficient to enable the image acquisition means to discriminate between colors.

35. Apparatus according to claim 34, wherein the image acquisition means is a video camera.

36. Apparatus according to claim 34, further comprising a transducer for applying pressure on said area, and for obtaining a signal value, which corresponds to maximum whitening of said area.

* * * * *